(12) United States Patent
Allmendinger (10) Patent No.: US 8,290,117 B2
(45) Date of Patent: Oct. 16, 2012

(54) CT IMAGE RECORDING OF A MOVING EXAMINATION OBJECT

(75) Inventor: Thomas Allmendinger, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 292 days.

(21) Appl. No.: 12/698,187

(22) Filed: Feb. 2, 2010

(65) Prior Publication Data
US 2010/0195889 A1 Aug. 5, 2010

(30) Foreign Application Priority Data
Feb. 4, 2009 (DE) .................... 10 2009 007 366

(51) Int. Cl.
*A61B 6/03* (2006.01)
(52) U.S. Cl. ................................. 378/8; 378/4
(58) Field of Classification Search .......... 378/4, 8; 382/128–132
See application file for complete search history.

(56) References Cited

U.S. PATENT DOCUMENTS

| | | | | |
|---|---|---|---|---|
| 6,639,965 | B1 * | 10/2003 | Hsieh et al. ................ | 378/8 |
| 7,187,745 | B2 | 3/2007 | Flohr et al. | |
| 2004/0120450 | A1 | 6/2004 | Flohr et al. | |
| 2007/0030946 | A1 * | 2/2007 | Tsuyuki et al. ............ | 378/8 |
| 2008/0219527 | A1 | 9/2008 | Lavi | |
| 2009/0092305 | A1 * | 4/2009 | Ditt et al. .................. | 382/131 |
| 2009/0202034 | A1 * | 8/2009 | Lauritsch et al. .......... | 378/4 |
| 2011/0142314 | A1 * | 6/2011 | Hsieh et al. ................ | 382/131 |

FOREIGN PATENT DOCUMENTS

DE 10245943 A1 4/2004
DE 102007046579 B3 * 1/2009

OTHER PUBLICATIONS

Hoffmann et al., Automatic determination of minimal cardiac motion phases for computed tomography imaging: initial experience, 2006, European Radiology, vol. 16, pp. 365-373.*

* cited by examiner

*Primary Examiner* — Toan Ton
*Assistant Examiner* — John Corbett
(74) *Attorney, Agent, or Firm* — Harness, Dickey & Pierce, P.L.C.

(57) ABSTRACT

A method is disclosed for scanning a moving examination object using a CT-System, with which data is captured during a circular movement of a transmitter/receiver pair through 360 degrees about the examination object, the data being assigned to the respective angular position. The 360 degrees are divided into n subsegments of equal size, where n is greater than 2, an even number and not divisible by 4. In at least one embodiment, the data assigned to the odd number subsegments forms a first data record and the data assigned to the even number subsegments forms a second data record. Differential information is determined between the first data record and the second data record. Motion information relating to the movement of the examination object is determined using the differential information.

28 Claims, 9 Drawing Sheets

FIG 9

CT IMAGE RECORDING OF A MOVING EXAMINATION OBJECT

PRIORITY STATEMENT

The present application hereby claims priority under 35 U.S.C. §119 on German patent application number DE 10 2009 007 366.3 filed Feb. 4, 2009, the entire contents of which are hereby incorporated herein by reference.

FIELD

At least one embodiment of the invention generally relates to a method for scanning a moving examination object using a CT system, with which data is captured during a circular movement of a transmitter/receiver pair through 360 degrees about the examination object.

BACKGROUND

Methods for scanning an examination object using a CT system are generally known. Circular scans, sequential circular scans with an advance system or spiral scans for example are used in this process. During these scans at least one transmitter/receiver pair, in other words an x-ray source and at least one x-ray detector opposite it, is used to record absorption data of the examination object from different recording angles and the absorption data captured in this manner is subjected to corresponding computation methods to produce sectional images through the examination object. Known reconstruction methods for determining sectional images are for example filtered back projection FBP, with which projections are transferred to a Fourier space where filtering is carried out and then after the data has been back transformed, a back projection to the sectional image level takes place. Another example of such a method is the SMPR method (SMPR=segmented multiple plane reconstruction), with which incomplete intermediate images are reconstructed from projection data over circle segments smaller than 180° and are then combined to form complete sectional images, for which it should be noted that the projection data used overall in this process has to be complementary to 180°- or 360° projection data.

One disadvantage of these generally known calculation methods is that if an examination object has moved or is moving, or if an examination object has moved at least partially, motion blur can result in the image, since during the time taken for a scanning process to acquire the data required for an image, there can be a locational displacement of the examination object or a part of the examination object, so that the data producing an image does not all reflect a spatially identical situation of the examination object. This motion blur problem is particularly acute when carrying out cardiac CT examinations on a patient, during which a significant motion blur can occur in the heart region due to the movement of the heart or for examinations, during which relatively fast changes in the examination object are to be measured.

SUMMARY

At least one embodiment of the invention specifies a method for scanning a moving examination object using a CT system. A corresponding CT system, a corresponding computer program and a corresponding computer program product are also to be presented.

With at least one embodiment of the inventive method, for scanning a moving examination object using a CT system, data is captured during a circular movement executed by a transmitter/receiver pair through 360° about the examination object, the data being assigned to the respective angular position. The 360° are divided into n subsegments of equal size, where n>2, an even number and not divisible by 4. The data assigned to the odd number subsegments forms a first data record and the data assigned to the even number subsegments forms a second data record. Differential information is determined between the first data record and the second data record. Motion information relating to the movement of the examination object is determined using the differential information.

The 360° movement about the examination object corresponds to the standard CT scanning procedure. This can take place either without the patient being advanced or as a spiral CT with such a patient advance. An assignment is carried out between the captured data and the scanning angle of the respective data capture so that for each data item the angular position at which the data was captured is known. The data is captured in the usual manner here, in that the transmitter emits x-ray radiation, this penetrates the examination object and the radiation attenuated by the examination object is detected by the receiver.

The division of the full 360° circle into n segments of equal size means that n sub data sets of equal size—or possibly at least roughly equal size—are present as a result of the assignment of the data to the angular position. Since n is an even number, the subsegments can be assigned to two halves, each half containing a total of 180°; this is done by allocating the odd number subsegments, i.e. the first, third, fifth, etc. subsegment, to a first data record and the even number subsegments, i.e. the second, fourth, sixth, etc. subsegment, to a second data record. If we look at the time sequence of the data capture, the data of the first and second data records therefore alternates. The condition that n is not divisible by 4 means that opposite each subsegment, i.e. with a 180° offset, is a subsegment of the other data record in each instance.

The differential information between the first data record and the second data record expresses a deviation of the first from the second data record. It can be calculated directly by linking the two data records; alternatively each data record can be processed beforehand and the differential information can then be determined as the difference between the processed data records.

The motion information is determined using the differential information between the first and second data records. This means that it is possible for further variables to be included in the determination of the motion information in addition to this differential information between the first and second data records. For example—as described in more detail below—differences can be taken into account not only between two but between a number of data records. Also a number of items of differential information, for example between the first and second data records, as well as between a third and the second data record, etc., can be included in the motion information.

In one development of an embodiment of the invention, a first image is reconstructed from the first data record, a second image is reconstructed from the second data record and the differential information between the first data record and the second data record is acquired as the difference between the first and second images. In this instance the difference is formed at image level, not at data record level.

The difference between the first and second images can also be determined by forming individual differences respectively between an individual image value of the first image and a corresponding individual image value of the second image. These image values can be the values of individual pixels of an image. Such individual differences are preferably calculated for all image values. The difference between the first and second images can then be determined by summing the individual differences. Whereas once the individual differences are formed, a number of variables, specifically the individual differences, are present, the number of which corresponds to the size of the images, a single variable results from summing as the measure of the difference.

According to one embodiment of the invention, the first and second data records are temporally adjacent and the motion information is determined using the differential information, in that both the differential information between the first data record and the second data record as well as the differential information between the second data record and a further data record temporally adjacent to the second data record is used. The temporal adjacency of the first and second data records comes about because the data of the odd and even number segments is not recorded simultaneously but consecutively; the temporal interval corresponds to the time taken for the transmitter/receiver pair to rotate through an angle of 360°/n.

Since the recording of data is not terminated after the rotation through 360° and thus the recording of the first and second data record, with further rotations of the transmitter/receiver pair instead taking place with simultaneous data capture, there are further data records, which follow on temporally from the second data record. The temporal displacement between the second and third, third and fourth, etc. data records, is the same time period in each instance, specifically the abovementioned rotation time of the transmitter/receiver pair through the angle of 360°/n. It is advantageous to determine the differential information of each data record in relation to its two adjacent data records and to use this variable to determine the motion information.

In one development of an embodiment of the invention the differential information is determined for a number of first and second data records, being captured at a number of times at the same level of the examination object. The result of this procedure is a temporal sequence of differential information, which is not location-dependent. Instead it relates to the same segment of the examination object, specifically a certain section through the examination object. The number of times is advantageously embodied so that they extend over a motion cycle of the examination object. The data records and thus the differential information are therefore available from the start to the end of the motion cycle. Such a motion cycle is present in particular when there is periodic movement of the examination object. One example of this is a cardiac phase. Another example is the respiratory movement of the lung and adjacent organs; their movement is considerably slower than the heart movement.

In one development of an embodiment of the invention differential information is determined for a number of first and second data records, being captured at different levels of the examination object, preferably at the same times within a motion cycle of the examination object. The various levels correspond after image reconstruction to different sections through the examination object. The result of this procedure is a spatial sequence of differential information, which is not time-dependent. The various levels preferably extend over the extension of the examination object or the part of the examination object that is of relevance for the image recording.

If we combine the described location and time-dependent determination of the differential information, we obtain a matrix of time and location-dependent differential information. In temporal space this preferably extends over a complete motion cycle and in locational space over the entire moving examination object.

In one embodiment of the invention the motion information indicates the strength of the movement of the moving examination object. The motion information can either be taken directly from the differential information or it results from an evaluation or further processing of the differential information. The motion information can in particular indicate the degree to which certain regions of the examination object move at certain times.

According to one example embodiment of the invention a time is determined on the basis of the motion information and is used to reconstruct an image of the examination object from the data. This is preferably a time, which is characterized by minor movement of the examination object. It can be a periodically recurring time, e.g. a particular cardiac phase.

One example embodiment of the inventive method is particularly advantageous for single-source devices, i.e. CT devices, which have only one transmitter and an associated receiver.

The number n, which corresponds to the number of subsegments, is preferably 18. But bigger or smaller numbers such as 10, 14, 22 or 26 are also possible. The selection of the number n is associated with defining the temporal interval between the data of the first and second data records. For a theoretical CT system with a rotation time of 150 ms, 10 or 14 segments would be advantageous, as then the temporal interval of roughly 20 ms between the data of the first and second data records matches the typical speeds in the heart of up to 10 cm/s. With a local resolution of around 0.6-0.8 mm these speeds produce a typical amplitude of 1-2 mm, which can be readily resolved.

The number n can also be determined as a function of the speed of the movement of the examination object. The number n then decreases as motion speeds reduce.

One example embodiment of the inventive CT system comprises a control and computation unit for Controlling the CT system, capturing detector data and reconstructing tomographic sectional images. It comprises a program memory for storing program code, with program code—in some instances also other items—being present therein, said program code being suitable for executing a method of the type described above during operation of the CT system.

The inventive computer program has program code segments or modules, which are suitable for implementing the method of at least one example embodiment of the type described above, when the computer program is executed on a computer.

One example embodiment of the inventive computer program product comprises program code means stored on a computer-readable data medium, said program code segments or modules being suitable for implementing the method of the type described above, when the computer program is executed on a computer.

BRIEF DESCRIPTION OF THE DRAWINGS

The invention is described in more detail below with reference to an example embodiment, wherein.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Figure 1:
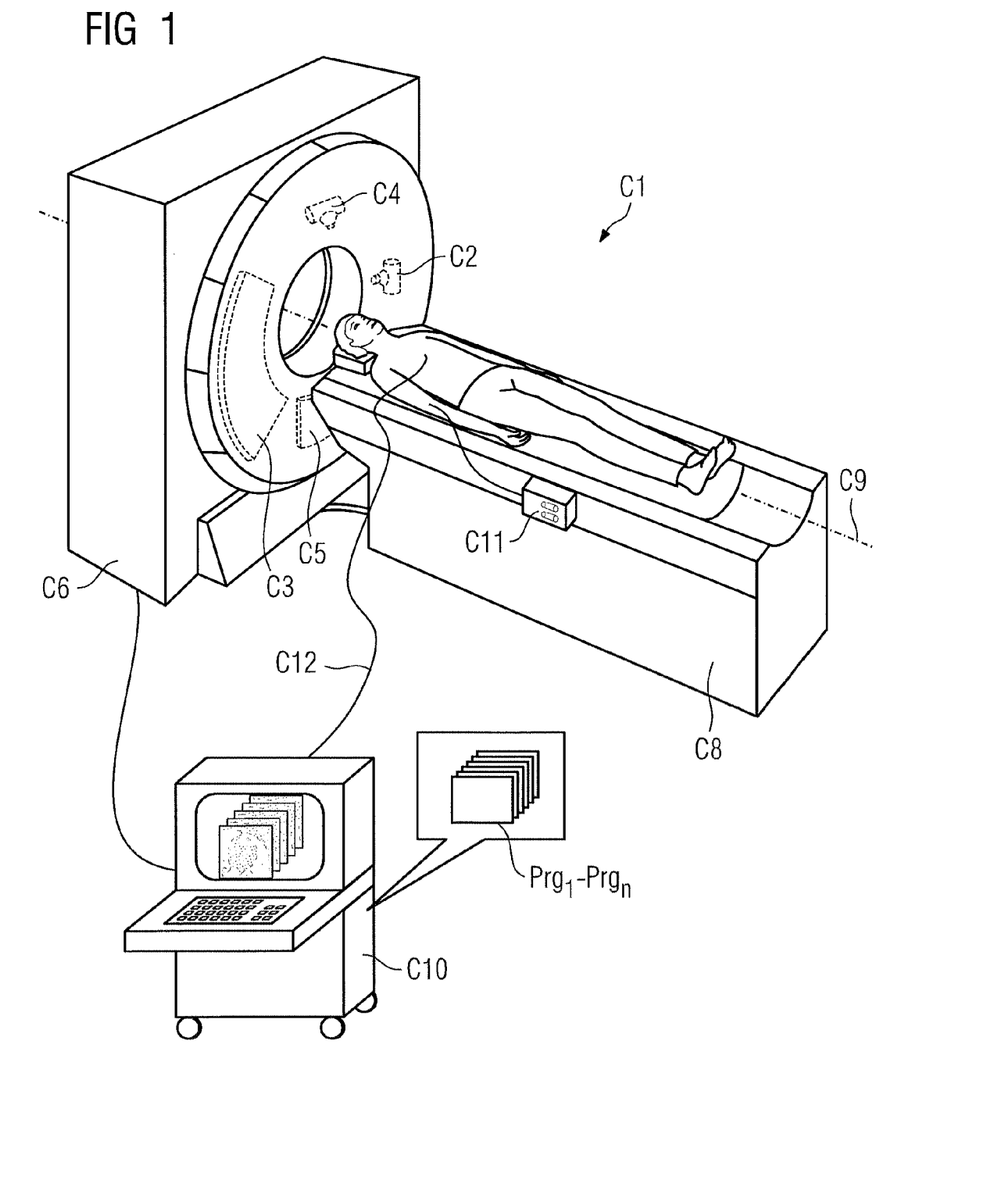
FIG. 1: shows a first CT system.

FIG. 1 shows a CT system C1 with a gantry housing C6, in which a closed gantry (not shown here) is present, on which a first x-ray tube C2 is disposed with a detector C3 opposite it. As an option in the CT system C1 shown here a second x-ray tube C4 is disposed with a detector C5 opposite it, so that a higher temporal resolution is possible with the additionally available emitter/detector combination or dual energy examinations can also be performed using different x-ray energy spectra in the emitter/detector systems. The CT system C1 also has a patient couch C8, on which a patient can be moved into the measuring field along a system axis C9, also referred to as the z-axis, during the examination.

The projection angle is changed by rotating x-ray tube C2 and optionally C4, and the detector C3 and optionally C5. Scanning can take place in the form of a purely circular scan without advancing the patient solely in the examination region of interest. Alternatively a sequential scan can be performed, in which the patient is moved gradually through the examination field between the individual scans. Alternatively it is of course also possible to perform a spiral scan, in which the patient is moved continuously along the system axis C9 through the examination field between the x-ray tube and detector during circumferential scanning with the x-ray radiation. The present CT system C1 is controlled by a control and computation unit C10 with computer program code $Prg_1$ to $Prg_n$ present in a memory. This control and computation unit C10 can also have the function of an ECG, with a line C12 being used to trace the ECG potentials between the patient and the control and computation unit C10.

The CT system C1 shown in FIG. 1 also has a contrast agent injector C11, by way of which contrast agent can also be injected into the blood circulation of the patient, so that the patient's vessels, in particular the ventricles of the beating heart, can be displayed more clearly. It is also possible here to carry out perfusion measurements, for which an embodiment of the proposed method is also suitable.

Figure 2:
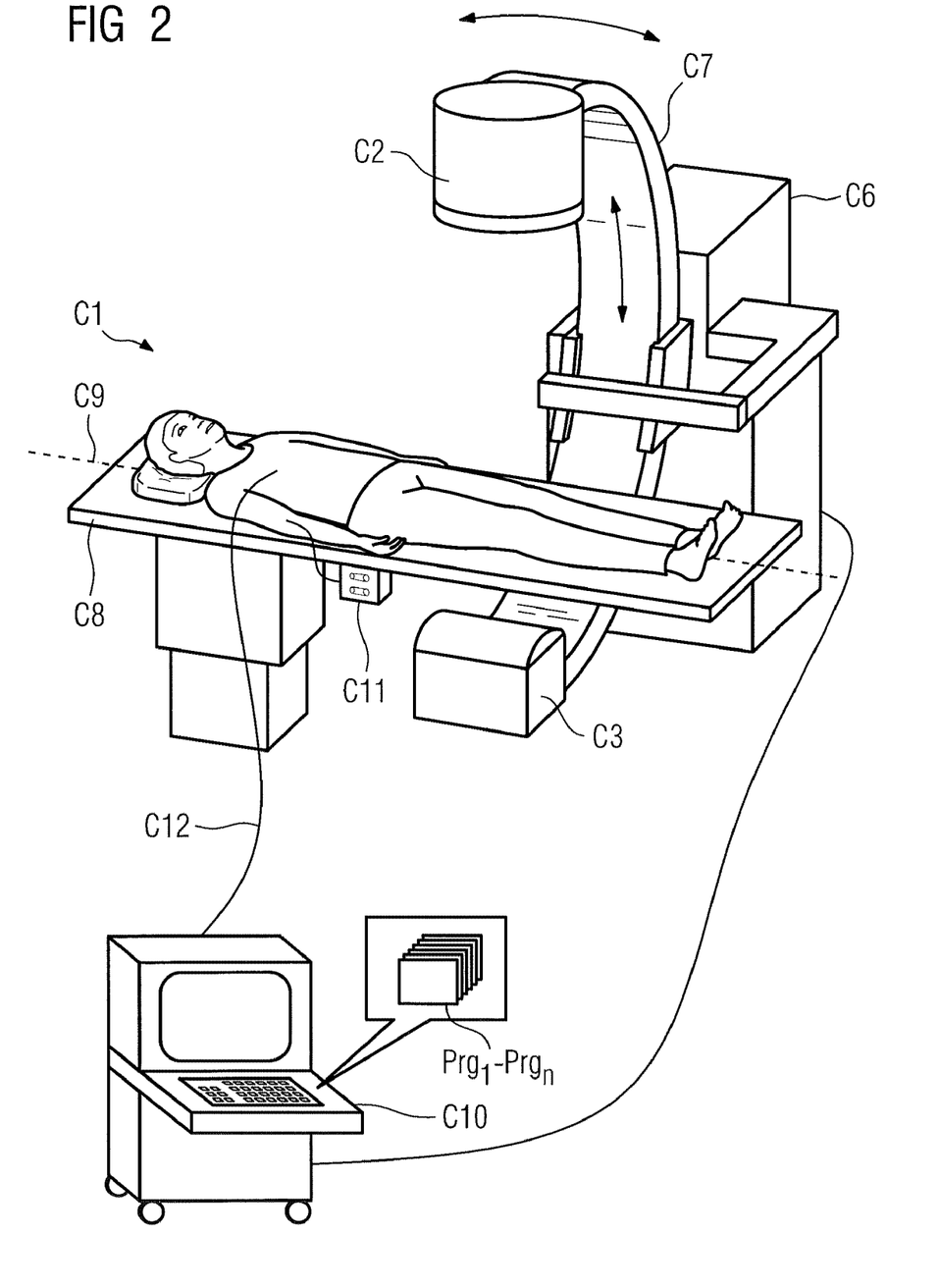
FIG. 2: shows a second CT system.

FIG. 2 shows a CT system C1 in the form of a C-arm system, in which in contrast to the CT system C1 in FIG. 1 the housing C6 supports the C-arm C7, to which both the x-ray tube C2 and the detector C3 opposite it are secured. The C-arm C7 is also pivoted about a system axis C9 for scanning, so that scanning can take place from a plurality of scanning angles and corresponding projection data can be determined from a plurality of projection angles. Like the CT system in FIG. 1, the C-arm system C1 also has a control and computation unit C10 with computer program code $Prg_1$ to $Prg_n$. This control and computation unit C10 can also be used to perform an ECG trace of the heart with the aid of an ECG line C12 and a contrast agent injector C11 can also be controlled by way of the control and computation unit C10, to administer an injection of contrast agent in the desired form to the patient on the patient couch C8.

Since in principle the same computation methods can be used to generate sectional images for both tomographic x-ray systems shown, the procedure described below can also be used for both systems.

The x-ray beam bundle emitted by the x-ray tube C2 passes through the patent and the x-ray beams reaching the detector C3 are detected during rotation at a plurality of projection angles. Each projection angle is therefore associated with captured data in the form of a projection or in the case of a multi-line detector C3 a number of projections corresponding to the number of detector lines.

The control and computation unit C10 uses the projections recorded during a reconstruction interval, which have been routed from the detector C3 to the control and computation unit C10, to reconstruct a sectional image of the examination object base on algorithms known per se. In order to be able to reconstruct meaningful sectional images, projections have to be recorded at projection angles, which extend over a reconstruction interval of at least 180°. In the following a reconstruction method is assumed, in which the projection data of half a circuit, in other words over projection angles of 0 to 180°, is to be used.

The above statement relating to the use of data from the projection angle range from 0 to 180° also applies to data in parallel geometry, i.e. in an arrangement in which all the beams strike the detector in a parallel manner. If measurements are taken using fan beam geometry, the parallel geometry can be acquired from the recorded data of the fan beam geometry by way of a simple transformation.

If parts of the body of the patient are to be recorded, which do not move or which stay still, recording the projections poses no significant problems. The recording of projections of a periodically moving object is however critical. One example of such an examination object is the human heart. The human heart is known to execute an essentially periodic movement. The periodic movement consists of an alternating sequence of a rest or relaxation phase and a movement or beat phase. The rest phase has a duration of generally between 500 to 800 ms, the beat phase a duration of 200 to 250 ms.

Figure 3:
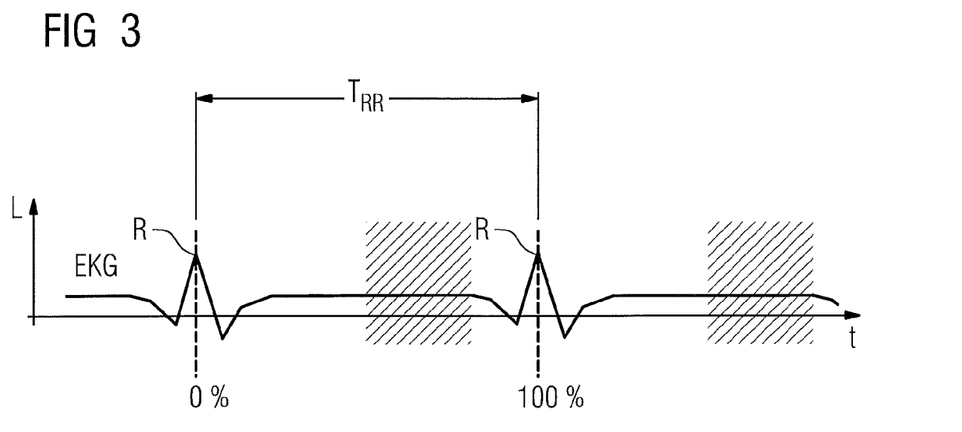
FIG. 3: shows a cardiac cycle.

This is shown in FIG. 3, where the level L of the ECG signal, shown as ECG, of a patient is plotted over time t. The ECG signal shows the periodic movement of the heart of the patient, the start of a cardiac cycle being determined respectively by an R wave R and the duration of the respective cardiac cycle by the RR interval $T_{RR}$, i.e. the interval between the R wave R initiating the cardiac cycle and the R wave R initiating the following cardiac cycle. A cardiac phase starts with an R wave R at 0% and ends with the next R wave R at 100%. Conversion between the dimension of time and the cardiac phase is possible at any time; the ECG data can be used for this purpose and it can be seen which cardiac phase is currently present at any time from this. The rest phase of the heart, i.e. the phase of minimal heart movement, is shown hatched in each instance.

Figure 4:
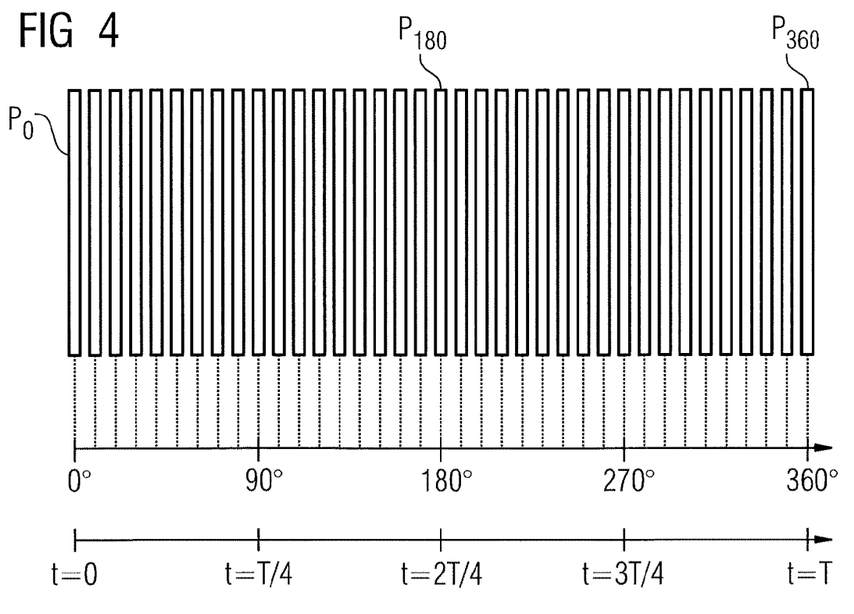
FIG. 4: shows data captured by a CT system.

During heart imaging using CT the cardiac phase in which data is acquired is a decisive factor for good image quality. Attempts are made for image reconstruction to use data which was captured during a cardiac phase with little or minimal heart movement. The following method can be used to determine a suitable phase:

Projections are recorded axially in the cardiac region and the corresponding sectional images are reconstructed from these. FIG. 4 shows a schematic diagram of projections $P_0$ to $P_{360}$, which are used later to reconstruct images. If the scan used as a basis here is a circular scan, the projection data shown here corresponds to the projection data of a specific detector line. If a spiral scan is performed, the projection data shown corresponds to the projections at a specific coordinate of the system axis, in other words a specific z-coordinate. It is possible here for absorption data from a number of lines to be used due to the advance in the z-direction during the spiral scan. The corresponding progressive projection angles between 0 and 360° are shown on the abscissa. An abscissa is also shown, on which the time profile is plotted for t=0 to t=T, where T corresponds to the rotation time for a full circuit of a scanning system about the examination object.

FIG. 4 is a simplified diagram for the purposes of clarity; normally scanning takes place with a smaller division than 1° steps. Therefore in contrast to the diagram in FIG. 4 in reality between at least 580, typically around 1160 projections are included in a sectional image.

Data is recorded for all cardiac phases and for the entire region of the z-axis, over which the heart or the part of the heart to be recorded extends.

Figure 5:
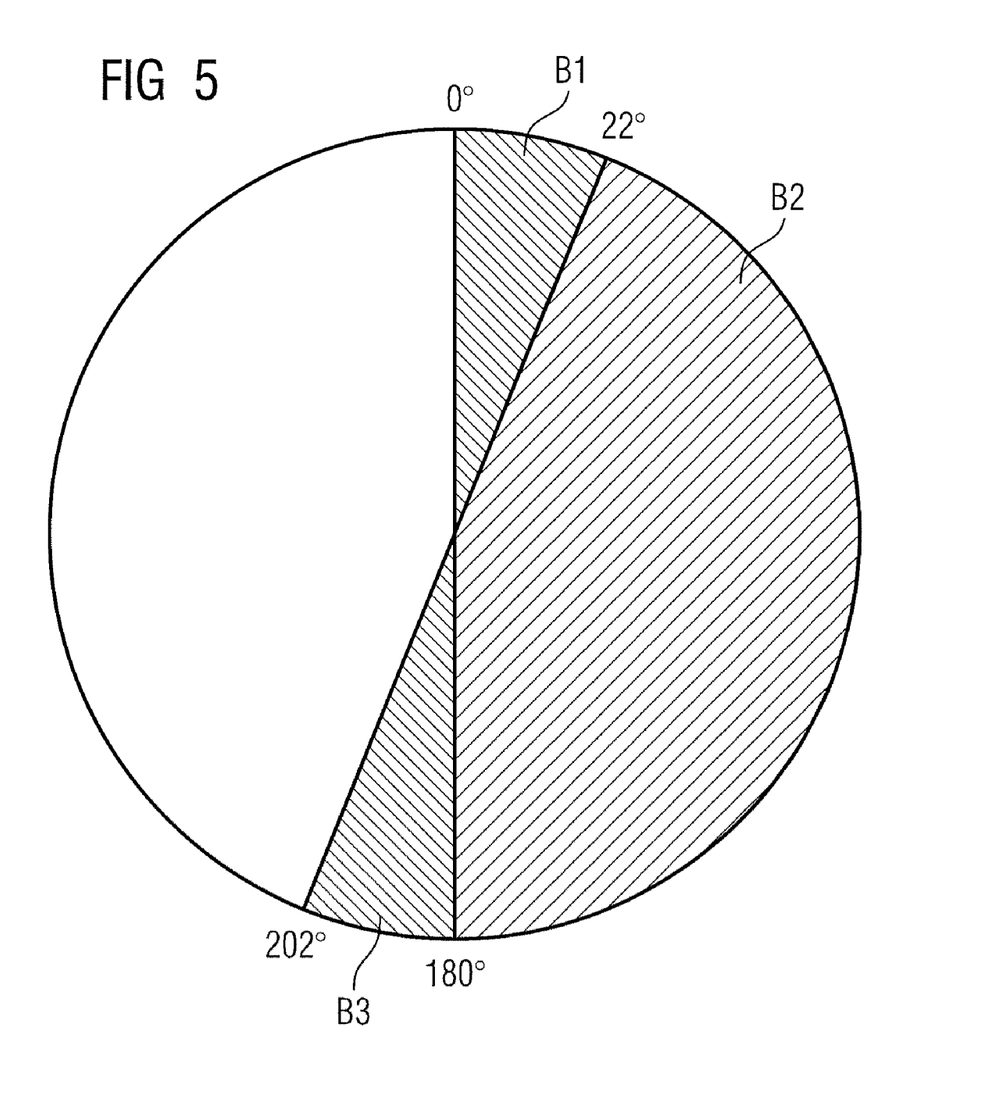
FIG. 5: shows a first assignment of data to images.

Data from a projection angle of 180° is used to reconstruct an image. This is shown in FIG. 5. The data recorded in the projection angle range between 0° and 180° is used for the first image. The data recorded in the projection angle range between 22° and 202° is used for the next image. For a rotation speed of the CT device of approximately 0.33 seconds/rotation this corresponds to a temporal progression of approximately 20 ms between the two images, corresponding to a cardiac phase progression of around 2%. Images are thus not continuously available for all cardiac phases but in steps of 2% of the cardiac phase. In other words images that are adjacent in the cardiac phase have a time difference of around 20 ms.

The result obtained after image reconstruction is a matrix of images I(p,z), where p stands for the cardiac phase or time of data capture and z for the z-position of the image, i.e. for a specific axial section through the heart. This matrix is used in the following, to determine the most favorable cardiac phase for data capture.

The differential values of the images of this z-position are formed for each z-position. This takes place as follows:

The differential value relating to the images of the same z-position and adjacent phase pn−1 and pn+1 is determined for each image I(pn,z) of the phase pn. To this end the difference is determined between the image and its one adjacent image of the phase pn−1, by first subtracting every pixel value of the image of the phase pn from the corresponding pixel value of the adjacent image of the phase pn−1 and then calculating the sum of the absolute differences of all the image pixels. Finally the result is divided by the number of image pixels. This is also done for the other adjacent image of the phase pn+1, so that a differential value is available for the image of the phase pn in relation to the adjacent image of the phase pn+1 and a differential value of the phase pn in relation to the adjacent image of the phase pn−1. These two differential values in relation to the two adjacent images are added together and the result forms the differential value of the image of the phase pn. Such a differential value is determined for a specific z-position for each phase value.

Alternatively it is also possible for the differential value of the image of the phase pn to be determined only in relation to one of its two neighbors, with the same neighbor, i.e. either the neighbor with the smaller or the neighbor with the larger phase, being used for each image.

The differential values are determined for all z-positions. The result is a two-dimensional motion matrix D(p, z) of differential values D, where p stands for the cardiac phase or time of data recording and z stands for the z-position of the image, i.e. for a specific axial section through the heart. Two such motion matrices D are shown in FIG. 6 by way of example. The z-position in mm is shown here on the x-axis and the time phase in ms on the y-axis. Each gray scale value corresponds to a specific differential value in the region between 0 and 8. Light regions show which heart regions demonstrate little movement at which time or in which cardiac phase. Conversely cardiac regions and times with more significant heart movement can be read from dark regions. As mentioned above, conversion between time and cardiac phase is possible at any time using the ECG information acquired during the CT data capture.

It is now possible to determine the cardiac phases, which—looking at the heart as a whole—correspond to minimum heart movement, by considering straight lines parallel to the x-axis and adding together the differential values along each straight line. The y-value of the straight line with the smallest resulting total value of the differential values corresponds to the cardiac phase with the smallest heart movement.

The following is a more complex procedure for determining the cardiac phases with minimal movement: the motion matrix D is determined for 12 cardiac cycles. The optimal cardiac phase is now determined separately for each individual cardiac cycle and a weighted mean is then used to determine an overall best phase.

Therefore the result of the imaging examination of the heart is that images which correspond to this favorable cardiac phase are provided. It is not necessary to capture new data for this purpose, nor do these images have to be reconstructed again; instead they are already available, as described above, within the matrix of images I(p,z). These images are selected after determination of the most favorable cardiac phase.

Alternatively it is also possible to calculate the images again, to achieve a higher resolution. It is thus possible for example to reconstruct the images with a resolution of 256× 256 to calculate the motion matrix D. The real clinical images should have a resolution of 512×512, so further reconstruction is expedient.

Figure 6A:
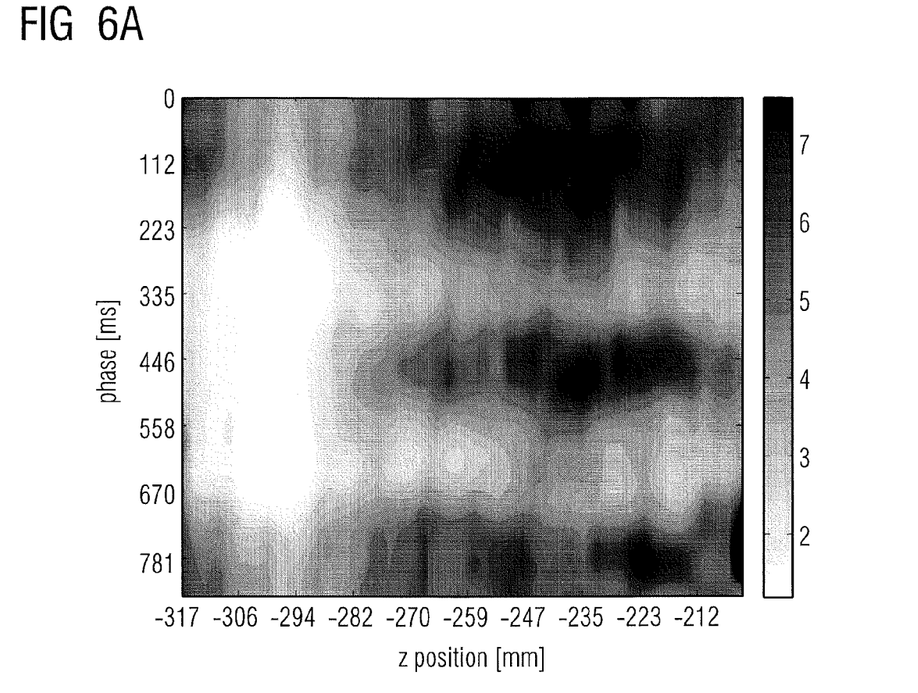
FIG. 6: shows two motion matrices.

The described procedure proves to be adequate for dual source devices, in other words devices which, as shown in FIG. 1, have two x-ray tubes C2 and C4 and two detectors C3 and C5 respectively opposite them. FIG. 6*a* thus shows a motion matrix determined on the basis of recordings of a dual source device. The high quality of the motion matrix is shown clearly, it being possible to distinguish cardiac regions and phases with significant movement clearly from those with little movement.

Figure 6B:
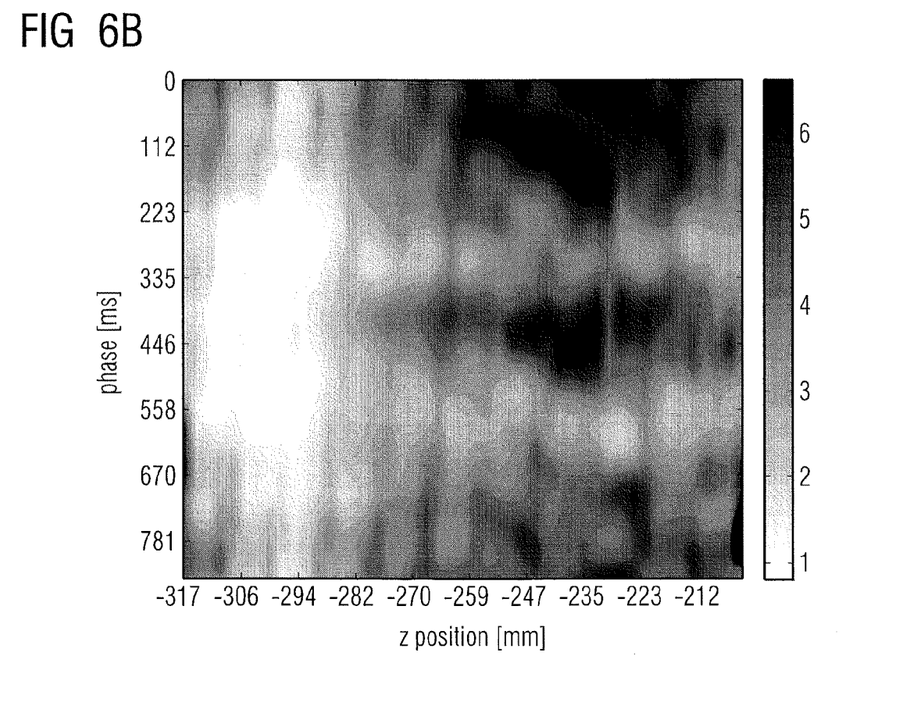

FIG. 6*b* in contrast shows a motion matrix of a single source device, in other words a device having only one x-ray tube C2 and a detector C3 opposite it. It can be seen here, in the left region of the image particularly, that the motion matrix demonstrates local minima and fluctuations of heart movement, which do not however correspond to reality. A deviation from reality can be concluded from the comparison of the two motion matrixes in FIGS. 6*a* and 6*b*. In FIG. 6*b* regions without movement are suggested, which do not exist in reality.

The unreliability of the motion matrix in FIG. 6*b* is due to the fact that when data is captured using a single source device certain heart movements are not perceptible. This is because when the heart moves essentially parallel to the current projection direction, the attenuation of the x-ray radiation is not changed. The opposite is true for a heart movement orthogonal to the projection direction. This means that with a single source device there is directional sensitivity in respect of the heart movement, which is reflected in the motion matrix. This is not the case with a dual source device, which, as shown in FIG. 1, has two x-ray tubes C2 and C4 aligned perpendicular to one another, as here every heart movement impacts on the attenuation of x-ray radiation, which is captured by at least one of the detectors C3 and C5.

This explanation also emerges from an analysis of FIG. 5. The data from the regions B1 and B2 is used to reconstruct the first image, while the data from the regions B2 and B3 is used to reconstruct the second image, corresponding to the somewhat later cardiac phase. Therefore largely identical data, specifically that of the region B2, is employed. If the differential value of the two images is formed, only the regions B1 and B3 have an impact. Therefore when forming the difference only data from a narrow angular range, specifically the two regions B1 and B3, is included. Heart movement in the region B2 is not taken into account when forming the difference. This means that it is possible only to determine a slight difference between adjacent images in the cardiac phase even with major heart movement.

It can also be determined that the poor quality of the motion matrices with single source devices increases as the heart rate increases.

Figure 7:
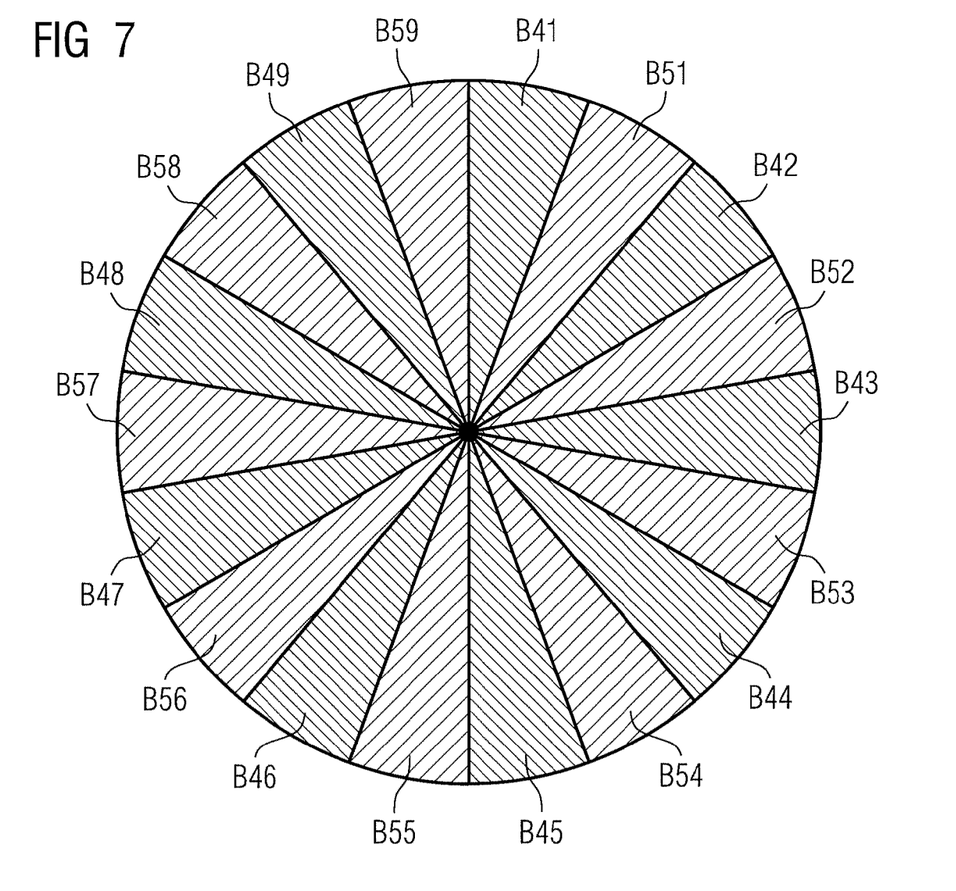
FIG. 7: shows a second assignment of data to images.

Given the above considerations, the following procedure is followed to increase the reliability of the motion matrices:

Data from a projection angle range of 180° is still used to reconstruct an image. This is shown in FIG. 7. However the full angular range of 360° is divided into 18 subregions of equal size. Data from the 9 subregions B41, B42, B43, B44, B45, B46, B47, B48 and B49 is used to reconstruct the first image and data from the 9 subregions B51, B52, B53, B54, B55, B56, B57, B58 and B59 is used to reconstruct the second image. In other words if the subregions are numbered continuously, the data from the odd number subregions is used for the first image and the data from the even number subregions is used for the second image. Viewed overall therefore a sector of 180° is scanned for the first and second images, so that a complete data record is available, which is adequate for reconstruction purposes.

The procedure in FIG. 5 is referred to below as method A, while the one in FIG. 7 is referred to as method B. In contrast to method A, according to method B the data of the first image and the second image does not overlap; it is disjoint. Therefore while according to method A there is a significant overlap of the data used, according to method B the data of the two images is statistically independent. Thus with method B heart movements in all directions are taken into account; the angle sensitivity occurring with single source devices and described above is not relevant. A heart movement is therefore captured more completely by forming the difference between the two images according to method B. The resulting motion matrix with method B has no artifacts as in FIG. 6*b*; this also applies with high heart rates.

Despite the independence of the data of the two images with method B, it has close temporal proximity. The temporal or cardiac phase interval between the two images corresponds to the length of a subregion and is calculated for a rotation speed of the CT device of 0.33 seconds/rotation at 0.33 seconds/18=18 ms. This corresponds to the resolution of the motion matrix.

Instead of dividing the full angular range of 360° into 18 subregions, as shown in FIG. 7, other divisions are also possible. These include sector formations with which the same number of subregions are available for both images, with an odd number of subregions being present for each image. All the subregions also have to be of equal size. These conditions are necessary because data from at least 180° has to be available for each image, with a projection angle of x° being equivalent to a projection angle of x+180°. Divisions into 6, 10, 14, 18, 22, etc. subregions are therefore possible. The higher the number of subregions, the greater the number of checkpoints on the motion matrix in the temporal direction. This impact on the temporal resolution of the motion matrix means that too small a number should not be selected. With 10 subregions the temporal interval between two adjacent images in the cardiac phase space would be 33 ms for a rotation time of 0.33 seconds for a full circuit, corresponding to a rough patterning or poor resolution of the motion matrix.

The number of subregions used can also be made a function of the motion speed of the examination object. If this is g in mm/s and the spatial resolution of the images is x in mm, then an appropriate number of subregions can be determined over t~x/g as the optimum temporal interval between adjacent subregions.

Data from the regions B42, B43, B44, B45, B46, B47, B48, B49 and one region B41 of the next rotation, etc. is used to reconstruct the third image. This means that the data of the second and third images also does not overlap. The same applies to all following images.

To avoid hard edges and edge artifacts in the images, weighted transitions are applied between the data to be used for a specific image and the data not to be used for it. A sinogram weighting in particular can be used for this purpose. Suitable weighting functions weight are shown in FIG. 8 as a function of the angle plotted on the x-axis in degrees.

Figure 8A:
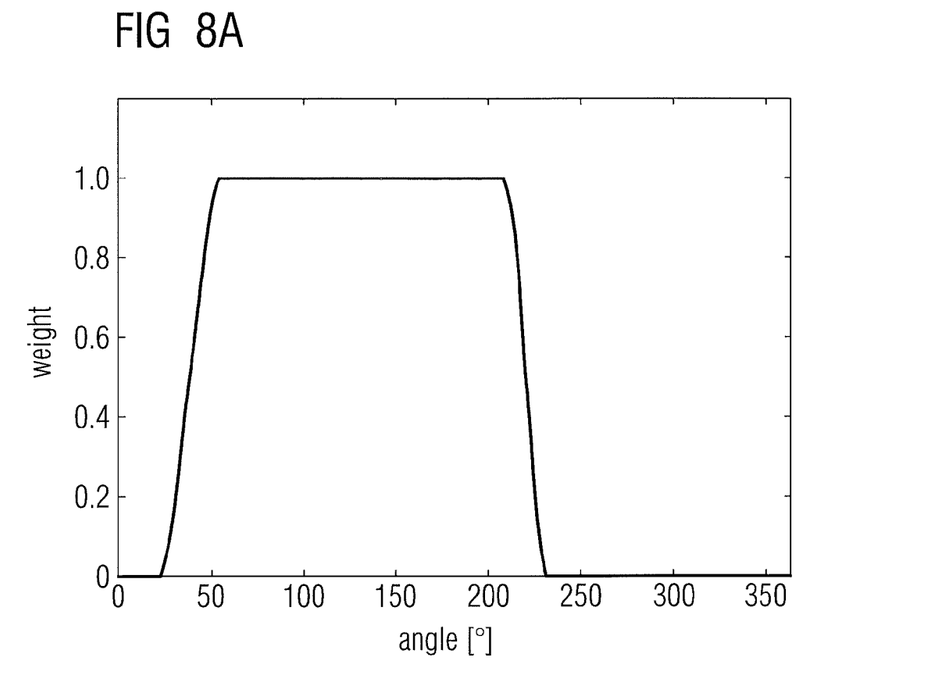
FIG. 8: shows weighting functions for selecting data to be used for image reconstruction.

FIG. 8a shows a weighting function weight, which is suitable for method A. A transition angle of approximately 30° is used here, so that data from a region 180°+30° can be included in an image. A weight rising between 0 and 1 is selected between 0° and 30°, for example a sin^2 function s(x) where) s(0°)=0 and s(30°)=1. Between 30° and 180° the weight is then constant=1. In the region between 180° and 210° the function 1−s(x) is used as the weight so that s(180°)=1 and s(210°)=0, to supplement the weights in the first 30° in a complementary manner to the sum 1, thereby producing a gentle transition.

Figure 8B:
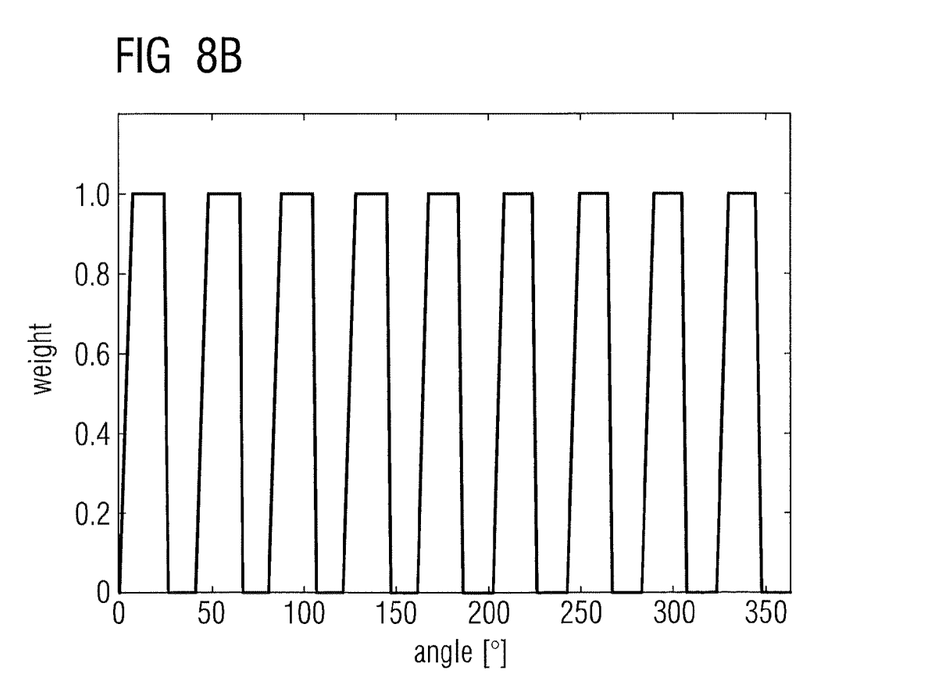

FIG. 8b shows a weighting function weight, which is suitable for the procedure according to method B. The segmentation into 9 regions is shown clearly. A transition angle of approximately 10° is used here. This softens the abovementioned statistical independence of the data from adjacent images in the cardiac phase space to some degree.

The procedure according to method B rather than the one according to method A only relates to the data selection for the purposes of reconstructing the images. The subsequent creation of the motion matrix and selection of the most favorable cardiac phase takes place as described above.

In particular both the image I(pn+1,z) and the image I(pn−1,z) can be used with method B to calculate the differential value of the image I(pn,z), as the data used to reconstruct both adjacent images I(pn+1,z) and I(pn−1,z) is independent of the data used to reconstruct the image I(pn,z).

Figure 9:
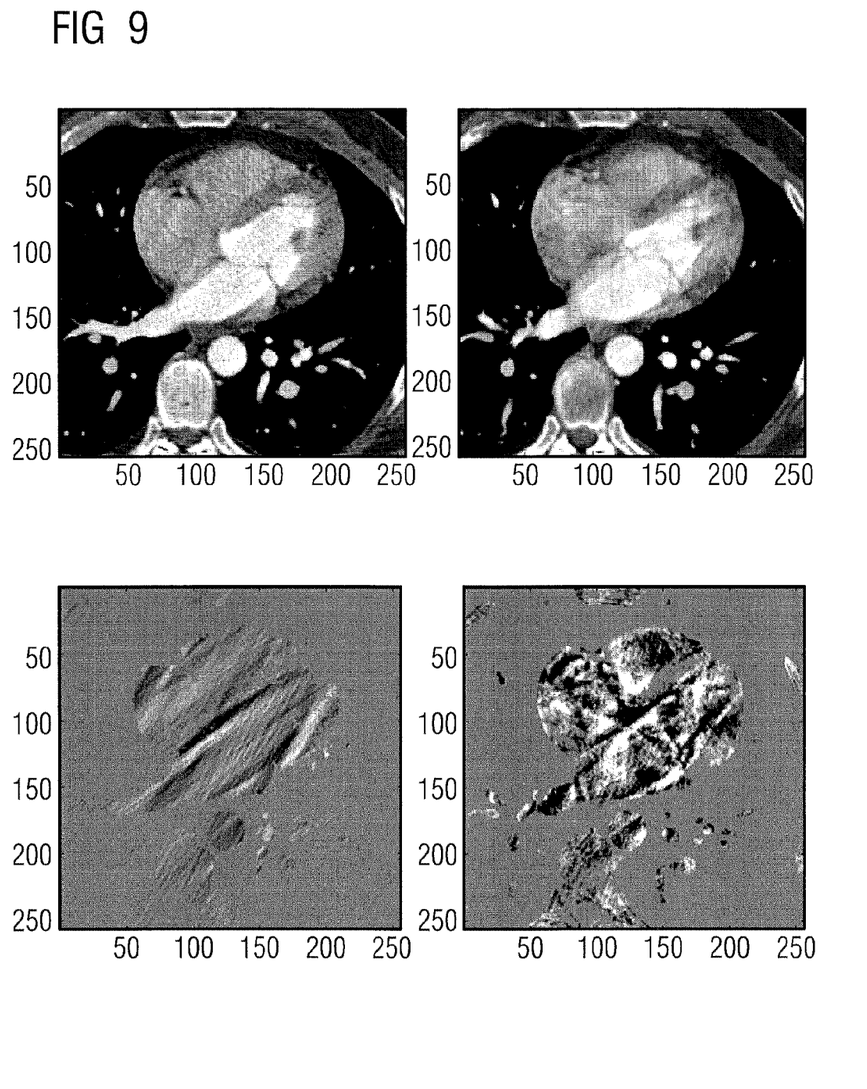
FIG. 9: shows CT images of a heart and differences between such CT images.

The qualitative difference between the methods A and B when using a single source device is clear from FIG. 9. The image top left is a cardiac image of a reconstruction using method A and bottom left the difference between two such images with 2% phase interval. The lines on the differential image are clearly visible. The lines indicate the preferred direction of heart movement to which the difference is sensitive. In contrast the image top right is a cardiac image of a reconstruction using method B and bottom right the difference between two such images with 2% phase interval. In this instance the differential image has no preferred direction; instead anatomical structures are visible here, which were produced by the movement of the heart.

The invention was described above with reference to one exemplary embodiment. It is evident that numerous changes and modifications are possible without departing from the scope of the invention. In particular—although the invention was described above using the example of heart examinations—other periodically moving body regions can also be examined using the described method.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for scanning a moving examination object using a CT-System, comprising:
    capturing data during a circular movement, of a transmitter/receiver pair of the CT-System, through 360 degrees about the examination object;
    assigning the captured data to a respective subsegments of angular position of the 360 degrees, the 360 degrees being divided into n subsegments of equal size, wherein n is greater than 2, is an even number and is not divisible by 4;
    forming a first data record from the data assigned to the odd number subsegments and forming a second data record from the data assigned to the even number subsegments;
    determining differential information between the first data record and the second data record; and
    determining motion information relating to movement of the examination object using the differential information.

2. The method as claimed in claim 1, wherein
a first image is reconstructed from the first data record, a second image is reconstructed from the second data record and
the differential information between the first data record and the second data record is acquired as a difference between the first and second images.

3. The method as claimed in claim 2, wherein
the difference between the first and second images is also determinable by forming individual differences respectively between an individual image value of the first image and a corresponding individual image value of the second image.

4. The method as claimed in claim 3, wherein
the difference between the first and second images is determined by summing the individual differences.

5. The method as claimed in claim 2, wherein
the first data record and the second data record are temporally adjacent, wherein the motion information is determined using the differential information, and wherein both the differential information between the first data record and the second data record, and the differential information between the second data record and a further data record temporally adjacent to the second data record, is used.

6. The method as claimed in claim 2, wherein
the differential information is determined for a number of first and second data records, being captured at a number of times at the same level of the examination object.

7. The method as claimed in claim 2, wherein
differential information is determined for a number of first and second data records, being captured at different levels of the examination object.

8. The method as claimed in claim 2, wherein
the differential information is determined for a number of first and second data records, being captured at different levels of the examination object, at the same times within a motion cycle of the examination object.

9. The method as claimed in claim 1, wherein
the first data record and the second data record are temporally adjacent, wherein the motion information is determined using the differential information, and wherein both the differential information between the first data record and the second data record, and the differential information between the second data record and a further data record temporally adjacent to the second data record, is used.

10. The method as claimed in claim 1, wherein
the differential information is determined for a number of first and second data records, being captured at a number of times at the same level of the examination object.

11. The method as claimed in claim 10, wherein
the number of times extends over a motion cycle of the examination object.

12. The method as claimed in claim 10, wherein
differential information is determined for a number of first and second data records, being captured at different levels of the examination object.

13. The method as claimed in claim 12, wherein
the various levels extend over the extension of the examination object.

14. The method as claimed in claim 13, wherein
a matrix of time and location-dependent differential information is created from the number of differential information items.

15. The method as claimed in claim 1, wherein
the differential information is determined for a number of first and second data records, being captured at different levels of the examination object, at the same times within a motion cycle of the examination object.

16. The method as claimed in claim 15, wherein
the various levels extend over the extension of the examination object.

17. The method as claimed in claim 1, wherein
the motion information indicates the strength of the movement of the moving examination object.

18. The method as claimed in claim 1, wherein
the motion information indicates the degree to which certain regions of the examination object move at certain times.

19. The method as claimed in claim 1, wherein
a time is determined on the basis of the motion information and is used to reconstruct an image of the examination object from the data.

20. The method as claimed in claim 19, wherein
the examination object is a heart and the time is a specific cardiac phase.

21. The method as claimed in claim 1, wherein
the CT system is a single source device with just one transmitter/receiver pair.

22. The method as claimed in claim 1, wherein n is equal to 18.

23. The method as claimed in claim 1, wherein n is equal to 10 or 14 or 22 or 26.

24. The method as claimed in claim 1, wherein n is determined as a function of the speed of movement of the examination object.

25. A CT system, comprising:
a control and computation unit for controlling the CT system, capturing detector data and reconstructing tomographic sectional images, the control and computation unit containing a program memory for storing program code, the control and computation unit being configured to execute program code to implement the method as claimed in claim 1.

26. A non-transitory computer-readable storage medium having computer-readable program code embedded therein configured to cause a computer to implement the method as claimed in claim 1, when the program code is executed on the computer.

27. The method as claimed in claim 1, wherein
differential information is determined for a number of first and second data records, being captured at different levels of the examination object.

28. A non-transitory computer readable medium including program segments for, when executed on a computer device, causing the computer device to implement the method of claim 1.

* * * * *